(12) United States Patent
Woo

(10) Patent No.: US 8,202,289 B2
(45) Date of Patent: Jun. 19, 2012

(54) DILATORS

(75) Inventor: Louis Woo, Alexandria, VA (US)

(73) Assignee: Smiths Group PLC, London (GB)

( * ) Notice: Subject to any disclaimer, the term of this patent is extended or adjusted under 35 U.S.C. 154(b) by 2765 days.

(21) Appl. No.: 10/685,809

(22) Filed: Oct. 16, 2003

(65) Prior Publication Data

US 2004/0087991 A1    May 6, 2004

Related U.S. Application Data

(60) Provisional application No. 60/422,480, filed on Oct. 31, 2002.

(51) Int. Cl.
*A61B 17/34* (2006.01)
*A61M 29/00* (2006.01)

(52) U.S. Cl. ........................................ 606/185; 604/104

(58) Field of Classification Search ............ 604/19, 604/96.01, 104, 264, 523; 606/108, 198, 606/185; 128/207.14, 207.15, 207.29
See application file for complete search history.

(56) References Cited

U.S. PATENT DOCUMENTS

| | | | | |
|---|---|---|---|---|
| 724,913 | A * | 4/1903 | Montgomery | 604/278 |
| 3,322,126 | A * | 5/1967 | Rusch et al. | 128/207.15 |
| 3,363,629 | A * | 1/1968 | Kuhn | 128/207.15 |
| 3,683,908 | A * | 8/1972 | Michael et al. | 128/207.15 |
| 3,769,983 | A * | 11/1973 | Merav | 128/207.15 |
| 3,794,026 | A * | 2/1974 | Jacobs | 128/200.13 |
| 3,880,168 | A * | 4/1975 | Berman | 128/207.15 |
| 3,968,800 | A * | 7/1976 | Vilasi | 606/198 |
| 4,033,353 | A * | 7/1977 | La Rosa | 128/207.15 |
| 4,211,234 | A * | 7/1980 | Fisher | 128/200.26 |
| 4,340,046 | A * | 7/1982 | Cox | 128/207.17 |
| 4,364,391 | A * | 12/1982 | Toye | 128/207.29 |
| 4,716,901 | A * | 1/1988 | Jackson et al. | 606/185 |
| 4,978,334 | A * | 12/1990 | Toye et al. | 604/506 |
| 5,058,580 | A | 10/1991 | Hazard | |
| 5,507,284 | A * | 4/1996 | Daneshvar | 128/207.14 |
| 5,546,936 | A * | 8/1996 | Virag et al. | 128/207.14 |
| 5,653,230 | A * | 8/1997 | Ciaglia et al. | 128/207.15 |
| 6,637,435 | B2 * | 10/2003 | Ciaglia et al. | 128/207.29 |
| 6,705,320 | B1 * | 3/2004 | Anderson | 128/207.14 |
| 2002/0004644 | A1 * | 1/2002 | Koblish | 604/104 |
| 2002/0066453 | A1 * | 6/2002 | Ciaglia et al. | 128/207.29 |
| 2002/0157665 | A1 * | 10/2002 | Igarashi et al. | 128/200.22 |
| 2003/0093105 | A1 * | 5/2003 | Huffmaster | 606/192 |
| 2004/0153120 | A1 * | 8/2004 | Seifert et al. | 606/200 |
| 2006/0100657 | A2 * | 5/2006 | Ciaglia et al. | 606/191 |

FOREIGN PATENT DOCUMENTS

| | | |
|---|---|---|
| DE | 100 65 604 | 7/2001 |
| FR | 2 808 990 | 11/2001 |
| GB | 2 379 393 | 3/2003 |
| JP | 5-506387 | 9/1993 |
| JP | 8-206220 | 8/1996 |
| WO | 92/14396 | 9/1992 |

* cited by examiner

*Primary Examiner* — Jackie Ho
*Assistant Examiner* — Michael J Anderson
(74) *Attorney, Agent, or Firm* — Louis Woo

(57) ABSTRACT

A tracheostomy dilator moulded from a plastics material is formed with an S shape having a flexible, tapered patient end region for insertion to the trachea. A handle region at the opposite end has a substantially constant diameter along its length. A passage along the dilator receives a guide member, the tip of the patient end of the dilator making a stepless transition with the surface of the guide member.

12 Claims, 2 Drawing Sheets

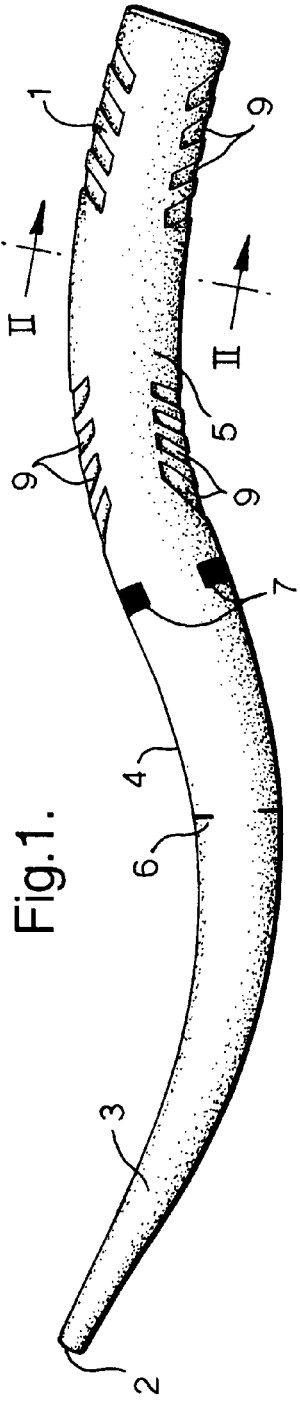
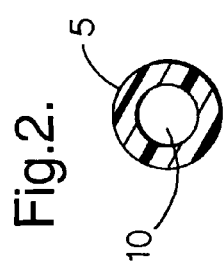
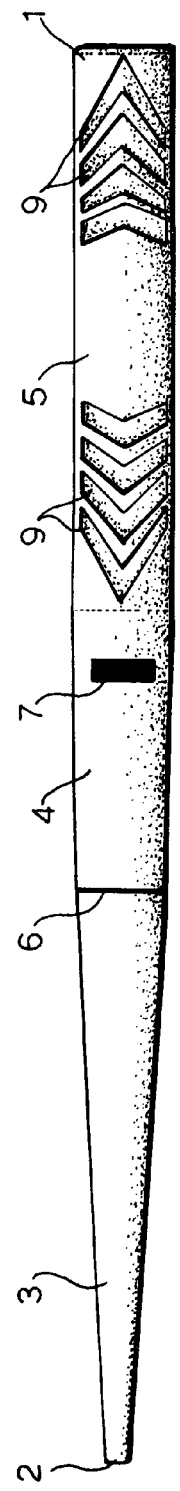

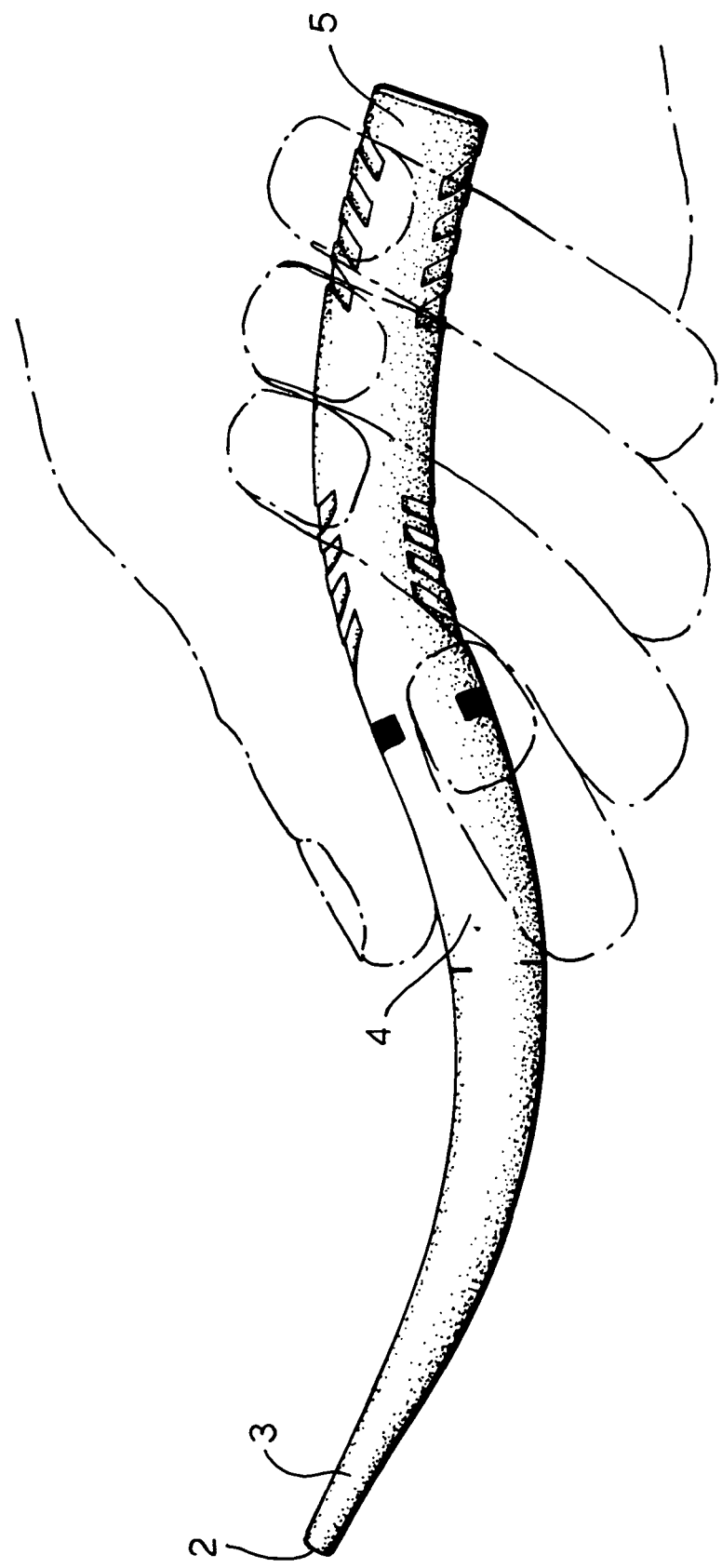

DILATORS

CROSS REFERENCE TO RELATED APPLICATION

This application claims priority of U.S. Provisional Application No. 60/422,480, filed on Oct. 31, 2002.

BACKGROUND OF THE INVENTION

This invention relates to dilators.

The invention is more particularly concerned with dilators used in forming a percutaneous tracheostomy.

Percutaneous tracheostomies can be formed in various ways. One technique involves the steps of inserting a hollow needle through the skin into the trachea, inserting a guidewire along the needle, withdrawing the needle over the guidewire and then using one or more dilators slid along the guidewire to expand the opening sufficiently to enable a tracheostomy tube to be inserted. Where a series of several dilators are used these have an increasing diameter so that the opening is gradually expanded. Alternatively, a single, more steeply tapered dilator can be used, as described in, for example U.S. Pat. No. 4,364,391, DE 10065604, U.S. Pat. No. 4,898,163 and U.S. Ser. No. 2002/0,066,453. The use of a single dilator is an advantage because it reduces the number of steps in the procedure and the number of components. One problem with this technique is that it can require some force to insert the dilator and this insertion must be performed in a carefully controlled manner to ensure that the dilator is not inserted too far.

BRIEF SUMMARY OF THE INVENTION

It is an object of the present invention to provide an alternative dilator.

According to one aspect of the present invention there is provided a tracheostomy dilator comprising a curved, tapered patient end region adapted for insertion through a tracheostomy to expand the tracheostomy as it is inserted and a handle region at an end of the dilator opposite the patient end region, the handle region being curved in an opposite sense from the patient end region.

According to another aspect of the present invention there is provided a tracheostomy dilator having one end providing a handle region and an opposite end providing a flexible, tapered patient end region for insertion to the trachea, the dilator being smoothly curved along substantially its entire length with an S shape.

The dilator preferably has a passage extending along it for receiving a guide member, and the tip of the patient end region may provide a substantially stepless transition with the surface of the guide member. The handle region preferably has a substantially constant diameter along its length and may have surface formations adapted to enhance grip. The dilator is preferably moulded from a plastics material, which may have a Shore hardness of substantially 90 A. The radius of curvature of the handle region may be substantially the same as that of the patient end region. The radius of curvature of the patient end may be about 90 mm. The dilator preferably has a coating of a hydrophilic material along its patient end region.

A dilator according to the present invention will now be described, by way of example, with reference to the accompanying drawings.

BRIEF DESCRIPTION OF THE DRAWINGS

FIG. 1 is a side elevation view of the dilator;
FIG. 2 is a cross-sectional view of the dilator along the line II-II of FIG. 1;
FIG. 3 is a plan view of the dilator; and
FIG. 4 illustrates how the dilator can be held in the hand.

DETAILED DESCRIPTION OF THE PREFERRED EMBODIMENT

With reference first to FIGS. 1 to 3, the dilator is a single piece, integral moulding of a stiff but flexible plastics material, such as polyurethane with a Shore hardness of 90 A. The overall length of the dilator is 193 mm and it has a circular section along its length, with a diameter of 13.65 mm at its rear end 1 and a diameter of 4.0 mm at the tip 2 of its forward or patient end.

The dilator has three regions along its length, a patient end or forward region 3, an intermediate region 4 and a handle or rear region 5.

The patient end region 3 extends for 80 mm and tapers along its entire length from a diameter of 4 mm at the tip 2 to a diameter of 12.85 mm at the rear end of the region. At the rear end of the patient end region 3 there is a marking 6 on the dilator to indicate the external diameter as being 38 FR.

The intermediate region 4 extends for 40 mm and has a much shallower taper along its length, the diameter at its rear end being 13.85 mm. Adjacent the rear end of this region 4 there is a thick marking 7 to indicate the maximum extent of insertion of the dilator.

The handle region 5 extends for 80 mm and is of constant diameter along its length. The handle region 5 is moulded with shallow chevron-shape ribs 9 to enhance grip.

The dilator is curved along substantially its entire length. Approximately the first 25 mm of the patient end region 3 is straight but the remainder of the patient end region and the intermediate region 4 is curved with a radius of about 90 mm. The handle region 5 is curved with a similar radius of curvature but in the opposite sense. These two curves give the dilator an overall S shape.

A passage 10 extends along the entire length of the dilator opening at both the rear end 1 and the patient end 2. The diameter of the passage 10 varies with the taper of the dilator, being 9 mm at the rear end 1 and 2 mm at the patient end tip 2. The wall thickness of the dilator reduces along the patient end region 3 as the dilator tapers to a reduced diameter.

Externally, the dilator is coated by dipping along its patient end and intermediate regions 3 and 4 with a hydrophilic coating, to aid insertion.

The dilator is preferably moulded in a straight or linear shape and is subsequently bent and retained in the desired shape. It is subjected to heat treatment followed by cooling to set it in this shape.

The dilator is used in the conventional percutaneous tracheostomy procedure. In this, a needle is first inserted through the skin into the trachea and a guidewire is inserted through the bore of the needle. The needle is removed, leaving the guidewire in position. A small-diameter guiding catheter is introduced over the guidewire and the dilator is then threaded along the guiding catheter and pushed through the opening into the trachea, expanding it as it is inserted up to about 38 FR. The guiding catheter has a diameter substantially equal to the diameter of the passage 10 at the tip 2. This, and the thin wall thickness of the dilator at this point ensures a substantially stepless transition between the guidewire and dilator, thereby facilitating insertion and reducing tissue trauma.

The dilator is then removed and a tracheostomy tube mounted on an introducer is slid into the trachea, through the expanded opening.

The curved shape of the dilator handle 5 has been found to give it ergonomic advantages and thereby overcome the problem of how to enable the user to apply a relatively high insertion force but in a controlled manner. The dilator could be held in different ways. Typically it might be held like a spoon, between thumb and forefinger, for the initial sliding along the guidewire and penetration of the skin surface. Thereafter, when additional force is required the user can shift his grip easily, as shown in FIG. 4, to hold the dilator like a trowel where the handle region 5 lies across the palm and is held against it by the little, ring and forefinger. The patient end region 3 of the dilator emerges from the hand between the thumb and the second joint of the forefinger and curves in the direction of the thumb. The thumb and forefinger provide the guidance and the other three finger provide the force. In this grip, the curve of the handle region 5 follows the shape of the palm grip allowing for a secure grip, which enables a well-controlled force to be applied.

Dilators according to the present invention may be used to expand a tracheostomy at various locations from the cricothyroid region to locations caudally along the trachea.

What I claim is:

1. A tracheostomy dilator comprising: a patient end region, said patient end region being curved, tapered and adapted for insertion through a tracheostomy to expand the tracheostomy as it is inserted; and a handle region at an end of the dilator opposite said patient end region, wherein said handle region and said patient end region are formed as a smooth continuous curve but in an opposite sense.

2. A dilator according to claim 1, wherein said dilator has a passage extending along it for receiving a guide member.

3. A dilator according to claim 2, wherein a tip of said patient end region provides a substantially stepless transition with an outer surface of said guide member.

4. A dilator according to claim 1, wherein said handle region has a substantially constant diameter along its length.

5. A dilator according to claim 1, wherein said handle region has surface formations adapted to enhance grip.

6. A dilator according to claim 1, wherein said dilator is moulded of a plastics material.

7. A dilator according to claim 6, wherein said plastics material has a Shore hardness of substantially 90A.

8. A dilator according to claim 1, wherein the radius of a curvature of said handle region is substantially the same as that of said patient end region.

9. A dilator according to claim 1, wherein the radius of curvature of said patient end is about 90 mm.

10. A dilator according to claim 1 including a coating of a hydrophilic material along its patient end region.

11. A tracheostomy dilator comprising one end providing a handle region and an opposite end providing a tapered patient end region for insertion to the trachea, wherein said dilator is smoothly curved along substantially its entire length with an S shape.

12. A tracheostomy dilator comprising: a patient end region, said patient end region tapering along its length; an intermediate region, said intermediate region tapering along its length substantially less than said patient end region; and a handle end region, said handle end region having a substantially constant diameter along its length, wherein said dilator has a passage extending within it and opening at a tip of said patient end region to accommodate a guide member along which said dilator is inserted to the trachea, wherein the wall thickness of said patient end region reduces towards a patient end tip such as to form a smooth transition with an outer surface of said guide member, and wherein said dilator is curved along substantially its entire length to an S shape so that the dilator can be held in the hand and inserted into the trachea ergonomically.

* * * * *